US00PP10205P

United States Patent [19]

Noodelijk

[11] Patent Number: Plant 10,205

[45] Date of Patent: Jan. 20, 1998

[54] CHRYSANTHEMUM PLANT NAMED 'SPLENDID REAGAN'

[75] Inventor: Robert Noodelijk, Woubrugge, Netherlands

[73] Assignee: Chrysanthemum Breeders Association, N.V., Netherlands

[21] Appl. No.: 738,605

[22] Filed: Oct. 29, 1996

[51] Int. Cl.[6] ..... A01H 5/00

[52] U.S. Cl. ..... Plt./74.1

[58] Field of Search ..... Plt./74.1, 82.4, Plt./82.5

*Primary Examiner*—Howard J. Locker

*Attorney, Agent, or Firm*—Parkhurst, Wendel & Burr, L.L.P

[57] ABSTRACT

A new and distinct cultivar of Chrysanthemum plant named Splendid Reagan, bearing small to medium sized purple blooms with a green center and performance of 24–28 days.

2 Drawing Sheets

The cultivar 'Splendid Reagan' as described and illustrated herein is related to the following cultivars:

'Dark Red Reagan' (U.S. Plant Pat. No. 9,929);
'Sunny Reagan' (U.S. Plant Pat. No. 9,928);
'Reagan' (U.S. Plant Pat. No. 8,642);
'Salmon Reagan' (U.S. Plant Pat. No. 8,869);
'Sulfur Reagan' (U.S. Plant Pat. No. 8,786);
'Dark Reagan' (U.S. Plant Pat. No. 8,966);
'Orange Reagan' (U.S. Plant Pat. No. 8,769);
'Bronze Reagan' (U.S. Plant Pat. No. 8,865);
'White Reagan' (U.S. Plant Pat. No. 8,784);
'Coral Reagan' (U.S. Plant Pat. No. 8,974);
'Yellow Reagan' (U.S. Plant Pat. No. 8,884);
'Dark Splendid Reagan' (U.S. Plant patent application Ser. No. 08/646,224); and
'Cream Reagan' (U.S. Plant patent application Ser. No. 08/738,606).

BACKGROUND OF THE INVENTION

The present invention comprises a new and distinct cultivar of Chrysanthemum plant which is a natural occurring sport of a parent Chrysanthemum named 'Reagan'. Parent Chrysanthemum 'Reagan' is described in U.S. Plant Pat. No. 8,642. The new cultivar was discovered as a whole plant mutation in 1990 in a greenhouse in Holland.

The invention has been asexually reproduced by cuttings at the same location. The new cultivar has been found to retain all of its distinctive characteristics through successive asexual propagations.

SUMMARY OF THE INVENTION

The present invention is a new and distinct variety of Chrysanthemum of a small to medium sized bloom and purple color.

BRIEF DESCRIPTION OF THE DRAWINGS

The present invention of a new and distinct variety of Chrysanthemum is shown in the accompanying drawings, the color being as nearly true as possible with color photographs of this type.

DESCRIPTION OF THE INVENTION

Figure 1:
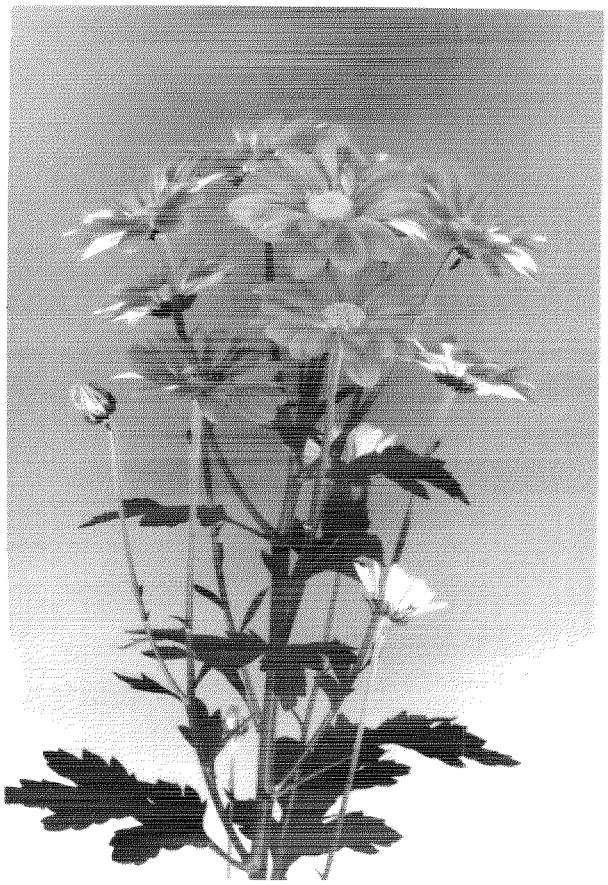
FIG. 1 shows the full bloom of the new cultivar.
Figure 2:
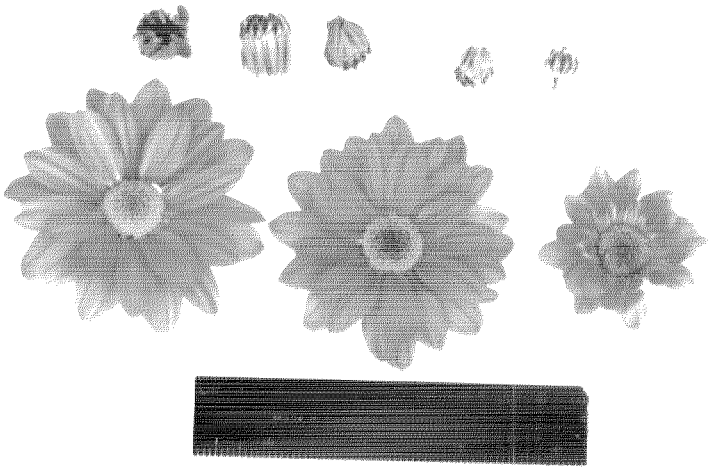
FIG. 2 shows the various stages of bloom of the new cultivar.
Figure 3:
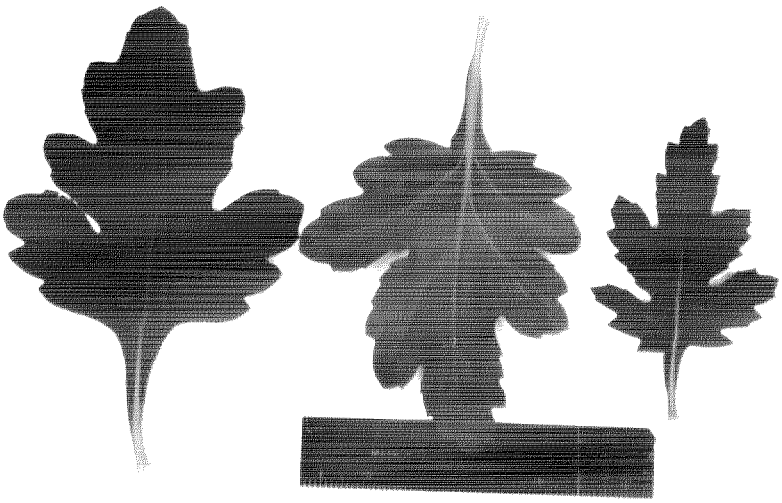
FIG. 3 shows foliage and petiole of the new cultivar.

This new variety of chrysanthemum is of the botanical classification *Chrysanthemum morifolium*. When grown in the vicinity of Ter Aar, Holland, it has a response time of approximately 7½ weeks. This new variety produces small to medium sized purple blooms with a green center having a 4 week performance (i.e., vase life of 24–28 days). This new variety of Chrysanthemum has been found to retain its distinctive characteristics throughout successive propagations and may be planted under greenhouse conditions in Holland between weeks 50 and 35.

The following is a description of the plant and characteristics (color designations are from The R.H.S. Colour Chart) that distinguish it from related known varieties and its antecedents. The color designations are taken from the plant itself. Accordingly, any discrepancies between the color designations and the colors depicted in the photographs are due to photographic tolerances.

Detailed Botanical Description and Comparative Data

| CULTIVAR | Splendid Reagan | Dark Splendid Reagan |
|---|---|---|
| Bud | | |
| Size | Medium cross section ±1.0 cm height ±0.7 cm | Medium cross section ±1.0 cm height ±0.7 cm |
| Form | Round and flat | Round and flat |
| Outside Color | Near Red-Purple 70A | Near Red-Purple 70A |
| Bloom | | |
| Size | Small to Medium | Medium |
| Fully Expanded | 6–6½ cm | 6½–7 cm |
| Borne | Upper portion, single flower per peduncle, lower portion plural flowers per peduncle | Upper portion, single flower per peduncle, lower portion plural flowers per peduncle |
| Peduncle Lengths | Near the top ±14 cm, near the middle ±24 cm, near the bottom ±28 cm | Near the top ±14 cm, near the middle ±24 cm, near the bottom ±28 cm |
| Peduncle Lateral Shoot, Attachment | Medium | medium |
| Peduncle Lateral Shoot, Angle | Medium | small |
| Form | Single (Daisy) | Single (Daisy) |
| Performance | Very good 24–28 days (18–20° C.) | Very good 24–28 days (19–20° C.) |
| Color | | |

-continued

Detailed Botanical Description and Comparative Data

| | | |
|---|---|---|
| Center of Flower | | |
| Mature | Yellow-Green 143B | Yellow-Green 144A |
| Immature | Yellow-Green 144C | Yellow-Green 154A |
| Base of Petals | Near Purple-Violet 80D but slightly more red | Near Red-Purple 71C but very slightly more blue |
| Outer Petals | Near Purple-Violet 80D but slightly more red | Near Red-Purple 71C but very slightly more blue |
| Inside of Petals | Near Purple-Violet 80D but slightly more red | Near Red-Purple 71C but bery slightly more blue |
| Reverse of Petals | Near Purple 75D but slightly deeper | Nearest Purple-Violet 80D but more grey and with a slightly deeper tesselation |
| Tonality from Distance | A purple daisy with a fresh looking center having a little or no pollen | A purple daisy with a fresh looking center having a little or no pollen |
| Discoloration | to Purple 75C | Some to Red-Purple 72C |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | Convex (no keels) | flat, no keels |
| Arrangement | Imbricated | Imbricated |
| Persistence | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium to large (1.5–2.0 cm) | Medium to large (1.5–2.0 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Medium | Medium |
| Height | 100–125 cm | 100–125 cm |
| Stem Color | Near Yellow-Green 146C | Yellow-Green 144A |
| Stem Strength | Medium | Strong |
| Stem Brittleness | Absent | Absent |
| Stem Anthocyanin Coloration | Present | Present, at the base and along the ribs |
| Internodes | 3–3½ cm | 3 cm |
| Flowering Response | 7½ weeks | 7½ weeks |
| Foliage | | |
| Color | Upperside green 147A. Underside Green 147B. | Upperside Green 137A. Underside Green 137C. |
| Size | Length ±11 cm. Width ±9 cm. | Length ±11 cm. Width ±9 cm. |
| Quantity | 22–28 | 22–28 |
| Shape | Lobed | Lobed |
| Texture | Upperside rough, underside smooth, slightly hirsute | Upperside rough, underside smooth, slightly hirsute |
| Ribs and Veins | Ribs well developed. Veins not so developed | Ribs well developed. Veins not so developed. |
| Edge | Crenated | Crenated |
| Shape of Base of Sinus Between Lateral Lobes | Round | Round |
| Margin of Sinus Between Lateral Lobes | Converging | Converging |
| Shape of Base | Truncate | Cordate |
| Apex | Mucronate | Mucronate |
| Growth | | |
| Differenee in average length | 0 | 0 |
| Response time | | |
| Differenee in days of average response | +1 | +½ |
| Response to ALAR | | |
| (g/100 l $H_2O$) | 300 | 300 |
| Year of Discovery | 1990 | 1991 |

| CULTIVAR | Dark Reagan | Dark Red Reagan |
|---|---|---|
| Bud | | |
| Size | Medium cross section ±1.0 cm height ±0.7 cm | Medium cross section ±1.0 cm height ±0.7 cm |
| Form | Round and flat | Round and flat |
| Outside Color | Between Greyed Purple 186A and B | Near Greyed Purple 186A |
| Bloom | | |
| Size | Medium | Medium |
| Fully Expanded | 6–6½ cm | 6½–7 cm |
| Borne | Upper portion, single flower per peduncle, lower portion plural flowers per peduncle | Upper portion, single flower per peduncle, lower portion plural flowers per peduncle |
| Peduncle Lengths | Near the top ±14 cm, near the middle ±24 cm, near the bottom ±28 cm | Near the top ±14 cm, near the middle ±24 cm, near the bottom ±28 cm |
| Peduncle Lateral Shoot, Attachment | Medium | Weak to medium |
| Peduncle Lateral Shoot, Angle | Medium | small |
| Form | Single (Daisy) | Single (Daisy) |
| Performance | Very good 24–30 days (18–20° C.) | Very good 24–28 days (18–20° C.) |
| Color | | |
| Center of Flower | | |
| Mature | Yellow-Green 151C | Yellow-Green 144A |
| Immature | Yellow-Green 154A | Yellow-Green 154A |
| Base of Petals | Red-Purple 69B lightly overlaid with Red-Purple 72A giving an overall impression of purple 75A but pinker | Unevenly colored; near Greyed-Red 182A lightly streaked with Greyed-Orange 167B |
| Outer Petals | Red-Purple 69B lightly overlaid with Red-Purple 72A giving an overall impression of purple 75A but pinker | Unevenly colored; near Greyed-Red 182A lightly streaked with Greyed-Orange 167B |
| Inside of Petals | Red-Purple 69B lightly overlaid with Red-Purple 72A giving an overall impression of purple 75A but pinker | Unevenly colored; near Greyed-Red 182A lightly streaked with Greyed-Orange 167B |

-continued

| Detailed Botanical Description and Comparative Data | | |
|---|---|---|
| Reverse of Petals | Red-Purple 69C with a light tesselation of Red-Purple 72A | Yellow-White 158A tinged with Greyed-Purple 186D between the ribs and towards the margin |
| Tonality from Distance | A pale bronze daisy with a fresh looking center having a little or no pollen | A red daisy with a fresh looking center having a little or no pollen |
| Discoloration | Some to Red-Purple 69C | Some to Greyed-Red 181C |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | flat, (two keels) | convex, two keels |
| Arrangement | Imbricated | Imbricated |
| Persistence | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium (1.5 cm) | Medium to large (1.5–2.0 cm) |
| Reproductive Organs | | |
| Stamen | Yellow, thick, 3 mm in length | Yellow, thick, 3 mm in length |
| Pollen | Appears at a late stage of blooming, yellow-orange in color | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Strong | Medium |
| Height | 100–125 cm | 100–125 cm |
| Stem Color | Yellow-Green 144A | Yellow-Green 144A |
| Stem Strength | Medium | Strong |
| Stem Brittleness | Present | Absent |
| Stem Anthocyanin Coloration | Present | Present, at the base and along the ribs |
| Internodes | 3 cm | 3 cm |
| Flowering Response | 7½ weeks | 7½ weeks |
| Foliage | | |
| Color | Upperside green 137A. Underside Green 137C. | Upperside Green 137B. Underside Green 137C. |
| Size | Length ±12 cm. Width ±9 cm. | Length ±11 cm. Width ±9 cm. |
| Quantity | 22–28 | 22–28 |
| Shape | Lobed | Lobed |
| Texture | Upperside rough, underside smooth, slightly hirsute | Upperside rough, underside smooth, slightly hirsute |
| Ribs and Veins | Ribs well developed. Veins not so developed. | Ribs well developed. Veins not so developed. |
| Edge | Crenated | Crenated |
| Shape of Base of Sinus Between Lateral Lobes | Round | Round |
| Margin of Sinus Between | Converging | Converging |

-continued

| Detailed Botanical Description and Comparative Data | | |
|---|---|---|
| Lateral Lobes | | |
| Shape of Base | Asymmetric | Cordate |
| Apex | Mucronate | Mucronate |
| Growth | | |
| Differenee in average length | 0 | 0 |
| Response time | | |
| Differenee in days of average response | +1 | +½ |
| Response to ALAR | | |
| (g/100 l $H_2O$) | 300 | 300 |
| Year of Discovery | 1990 | 1992 |

| CULTIVAR | Parent Cultivar Reagan |
|---|---|
| Bud | |
| Size | Medium cross section ±1.0 cm height ±0.7 cm |
| Form | Round and flat |
| Outside Color | Near Greyed Purple 186A |
| Bloom | |
| Size | Medium |
| Fully Expanded | 6½–7 cm |
| Borne | Upper portion, single flower per peduncle, lower portion plural flowers per peduncle |
| Peduncle Lengths | Near the top ±14 cm, near the middle ±24 cm, near the bottom ±28 cm |
| Peduncle Lateral Shoot, Attachment | Medium |
| Peduncle Lateral Shoot, Angle | Medium |
| Form | Single (Daisy) |
| Performance | Very good 24–28 days (18–20° C.) |
| Color | |
| Center of Flower | |
| Mature | Yellow-Green 151C |
| Immature | Yellow-Green 154A |
| Base of Petals | Purple 75B |
| Outer Petals | Purple 75B |
| Inside of Petals | Purple 75B |
| Reverse of Petals | Red-Purple 69D but paler |
| Tonality from Distance | A pale pink daisy with a fresh fresh looking center having a little or no pollen |
| Discoloration | Some to Red-Purple 69D |
| Pollen | Yellow-Orange 14A |
| Petals | |
| Texture | Upperside smooth, underside smooth |
| Number | 24–30 (two rows) |
| Cross-section | flat, (two keels) |
| Arrangement | Imbricated |
| Persistence | Good. Petals keep straight or reflex somewhat at the edge at the end of blooming. |

-continued

| Detailed Botanical Description and Comparative Data | |
|---|---|
| Fragrance | Typical Chrysanthemum |
| Disc Diameter | Medium (1.5 cm) |
| Reproductive Organs | |
| Stamen | Yellow, thick, 3 mm in length |
| Pollen | Appears at late stage of blooming |
| Styles | Green, thick |
| Style Length | ±5 mm |
| Stigmas | Yellow |
| Stigma Width | ±1 mm |
| Ovaries | Enclosed in calyx |
| Plant | |
| Form | Spray mum meant for erect culture. Herbaceous. |
| Growth | Strong |
| Height | 100–125 cm |
| Stem Color | Yellow-Green 144A |
| Stem Strength | Medium |
| Stem Brittleness | Present |
| Stem Anthocyanin Coloration | Absent |
| Internodes | 3 cm |
| Flowering Response | 7½ weeks |
| Foliage | |
| Color | Upperside green 137A. Underside Green 137C. |
| Size | Length ±12 cm. Width ±9 cm. |
| Quantity | 22–28 |
| Shape | Lobed |
| Texture | Upperside rough, underside smooth, slightly hirsute |
| Ribs and Veins | Ribs well developed. Veins not so developed. |
| Edge | Crenated |
| Shape of Base of Sinus Between Lateral Lobes | Round |
| Margin of Sinus Between Lateral Lobes | Converging |
| Shape of Base | Rounded |
| Apex | Cuspidate |
| Growth | |
| Differenee in average length | 0 |
| Response time | |
| Differenee in days of average response | +0 |
| Response to ALAR | |
| (g/100 l $H_2O$) | 300 |
| Year of Discovery | 1986 |

I claim:

1. A new and distinct variety of Chrysanthemum plant as described and illustrated.

* * * * *